United States Patent [19]

Bottcher et al.

[11] Patent Number: 5,439,863
[45] Date of Patent: Aug. 8, 1995

[54] NEUTRAL METAL COMPLEX SALTS

[75] Inventors: Axel Bottcher, Wesel; Manfred Doring, Jena; Jürgen Zehrfeld, Voerde, all of Germany

[73] Assignee: Rutgerswerke Aktiengesellschaft, Germany

[21] Appl. No.: 119,026

[22] Filed: Sep. 9, 1993

[30] Foreign Application Priority Data

Sep. 22, 1992 [DE] Germany .................. 42 31 622.7

[51] Int. Cl.⁶ .............................................. C07F 15/00
[52] U.S. Cl. ........................... 502/152; 502/155; 502/156; 502/167
[58] Field of Search ............... 502/152, 155, 156, 167

[56] References Cited

U.S. PATENT DOCUMENTS

| | | | |
|---|---|---|---|
| 3,792,016 | 2/1974 | Hill et al. | 528/92 |
| 4,008,260 | 2/1977 | Kunstle et al. | 556/40 |
| 4,101,514 | 7/1978 | Thom | 528/109 |
| 4,105,667 | 8/1978 | Thom | 548/101 |
| 4,337,210 | 6/1982 | van der Maas | 556/40 |
| 4,338,254 | 7/1982 | van der Maas | 556/40 |
| 4,617,408 | 10/1986 | Nestler et al. | 502/152 |
| 4,621,150 | 11/1986 | Hirai et al. | 502/167 |

FOREIGN PATENT DOCUMENTS

| | | |
|---|---|---|
| 2075880 | 10/1971 | France . |
| 292463 | 8/1991 | German Dem. Rep. . |
| 3201381 | 9/1982 | Germany . |

*Primary Examiner*—Asok Pal
*Assistant Examiner*—Walter D. Griffin
*Attorney, Agent, or Firm*—Bierman and Muserlian

[57] ABSTRACT

Neutral metal complex salts with additional ligands acting as bases and a process for their preparation and their use as latent polymerization catalysts for the production of pre-cured products which can be further cured without another curing catalyst.

14 Claims, No Drawings

NEUTRAL METAL COMPLEX SALTS

STATE OF THE ART

The literature is replete with a plurality of different organo-metallic complex compounds useful as catalysts, accelerators, initiators and the like for organic reactions. Recently, chelate complexes of the transition metals with diketones, dithiocarbamide acid derivatives, dihydroxy compounds, diamines or other difunctional ligands, have particularly gained importance as catalysts for polymerization and curing reactions. The production of such simple neutral transition complexes is described for example in U.S. Pat. Nos. 4,337,210, No. 4,338,254, No. 4,008,260 and No. 4,279,829.

Transition complexes in which ligands of different types are coordinated around a central atom, until now had been produced in complicated processes, wherein dry, solvent-free transition metal complexes produced in a first step are coordinated in a second process step with additional ligands, such as for example pyridine, butylamine or benzylamine (Olszewski et al, J. Inorg. Nucl. Chem. Vol. 27, pgs. 1043–1048 (1965).

Processes have also been described by which mixed coordinated complexes of this type can be produced in a single-step process, but for carrying them out, expensive transition metal acetates are required. In addition, yields fluctuating greatly between 20 and 88% are obtained so that carrying out the process on a commercial scale has proven to be uneconomical (Bereman et al, Inorg. Chim. Acta, Vol. 130, pgs 195–201) (1987). It is also known to use a single-step process from publication DD-A5-292 463. However, in this process, work must take place in expensive organic solvents or mixtures in the presence of organic auxiliary bases such as tributylamine or other tertiary amines. In this process, the effect of the solution behavior of the complexes formed is disadvantageous. Since the neutral complexes obtained are partially soluble in the solvents used, losses of the yield must be accepted which cannot be compensated for by concentration. Moreover, the accumulating quantities of impure solvents must be disposed of or must be reprocessed and the same applies for the ammonium salts generated as by-products. It is also a disadvantage of this process that precisely these ammonium salts which are partially odor-intensive adhere in small amounts in the end product and require additional purification.

But not only is the production of previously known organo-metallic complex compounds afflicted with shortcomings, but also in their use as polymerization or curing catalysts for the production of high-quality products occur problems which until now could only be solved reasonably through the addition of further additives or through a complicated time intensive temperature and pressure guidance. If, for example, the addition products known from U.S. Pat. No. 4,487,914 as comprising imidazole or substituted imidazoles, an epoxy compound and a metal salt are used as curing catalysts for epoxy reins, extremely strong temperature increases occur during the reaction which lead to discoloration of the products, to partial carbonization and to inhomogeneities in the cured material.

The addition of solvents to decrease the high reactivity after the onset of the polymerization reaction, as described in DE-OS 2, 810,428, also does not lead to a satisfactory solution since the subsequent removal makes necessary additional processing steps and the cured products show undesirable hollow spaces which increase their capacity to absorb water or other solvents. The increased fluid absorption capacity results in a significant deterioration of the electrical and mechanical properties of the polymer.

While the imidazole metal complexes of U.S. Pat. Nos. 3,638,007, 3,792,016 and 4,101,514 and DE 2,300,489 as latent curing agents become only active at temperatures above 170° C. and split off imidazole, and therewith cause reduced product qualities through undesirable side reactions, it is possible to produce with the neutral metal complexes known from PCT/WO 91/00419, polymer mixtures which are stable at room temperature and storable, which, however, are already cured to form high-quality products at temperatures above 50° C. However, the disadvantage of these catalysts is that after the onset of the reaction, the complete curing takes place directly. A stepwise curing which, for example, would permit the production of storable prepregs utilizing only one single curing system is not possible.

OBJECTS OF THE INVENTION

It is an object of the invention to provide a simple and environmentally safe process for the production of neutral transition metal complex salts from economical metal salts in a one-step process in an aqueous medium without costly purification or processing steps.

It is another object of the invention to provide novel neutral metal complex salts with ligands having different chemical structures coordinated about a central atom in substantially quantitative yields and high purity without costly purification steps.

It is a further object of the invention to provide novel curing catalysts for a curable polymer mixture with a curing latency stable at room temperature, partially curable at slightly increased temperatures to simply produce pre-cured intermediate products which will cure at increased temperatures after having been given their fixed form.

These and other objects and advantages of the invention will become obvious from the following detailed description.

THE INVENTION

The novel process of the invention for the preparation of a neutral metal complex salt with additional coordinated ligands comprises reacting a complex-forming metal salt of the second and third main groups of the Periodic Table of elements and sub-groups thereof with a chelating ligand and a Lewis base in water and an inorganic auxiliary base which forms a soluble salt with the acid of the metal salt and the optional presence of a solubilizer in stoichiometric amounts while inputting high energy to form the neutral complexes and recovering the product in fine crystalline form, the reaction being effected by the equation:

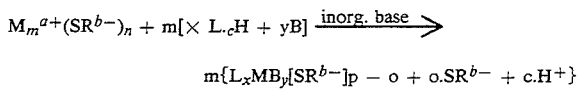

$$m\{L_xMB_y[SR^{b-}]_p - o + o.SR^{b-} + c.H^+\}$$

wherein M is a metal ion, SR is an acid radical of an organic or inorganic acid, B is a Lewis base and L is a chelating ligand, wherein $$m \cdot a = b \cdot n \geqq m(c \cdot x),$$

$$x \cdot c \leqq a \text{ and } b = p, m \cdot o \leqq p, \text{ and}$$
$$m$$

a=an integer of 1–8,
b=an integer of 1–3,
c=an integer of 0–4,
m=an integer of 1–3,
n=an integer of 1–8,
o=an integer of 0–8,
x=an integer of 0–4,
y=an integer of 8–15.

The use of organic auxiliary bases is widely used in organic chemistry. For the synthesis of acid amides or esters, for example, an auxiliary base is required which can often simultaneously serve as a solvent or as the reaction medium. Due to the stearic and electronic influences, this has a very different effect on the achieved yields and purities of the products.

It has now been found that through the use of inorganic auxiliary bases such as NaOH, KOH, Ca(OH)$_2$, Mg(OH)$_2$ or basic salts, such as sodium acetate, sodium carbonate or potassium carbonate, sodium bicarbonate, CaCO$_3$ in water, which potentially in the event of insolubility of the chelating ligand or the ligand to be bound and acting as Lewis bases, is mixed with a solubility enhancer or solubilizer, such as alcohol, from metal salts in the presence of various complexing agents are formed metal complexes having low solubility, particularly such with a high ligand number or mixed coordinated metal complexes which are precipitated with a nearly quantitative yield and especially high purity while the cations of the auxiliary bases used form water-soluble salts and stay in solution.

It has furthermore been found that through a high energy input, brought about by the effect of high shear forces which occur with an extremely high stirrer speed or in the dissolver, the formation of the complexes themselves as well as of the precipitating crystals are strongly accelerated. The input of the energy can also take place through the effect of ultrasound, microwaves or a laser beam. While the precipitation of the complex salts conventionally occurs only after a given waiting period, the complexes formed in this way can be immediately separated so that their production can take place in a continuous process.

It has also been found that these neutral metal complexes partially release Lewis bases under the influence of energy and consequently, the curing of an epoxy resin can be implemented so as to take place in stages.

As complexing agents can be used uncharged, simple Lewis bases with a free electron pair or multitoothed chelating agents which means compounds which can occupy more than one coordination site on the central atom. They can be used alone or in mixtures, and in the latter cases, complexes are formed in which the central metal ion is not only coordinated by one type of ligand but rather is mixed to obtain identical, mixed coordinated complexes with, in each instance, the same molar ratio of the complexing agents used. It is advantageous that these complexes can be precipitated in a single-stage process from aqueous solutions and that after their separation, excess mother lye is obtained which can be processed in a simple manner or, after the precipitation of the salts, can be used again or can be used directly again.

It is of particular advantage that through the use of inorganic bases, uniform odorless complexes with high purity and high yields are reproducibly obtained. They have a fine powdery consistency and when used as latent curing accelerators for epoxy resins, can be readily apportioned even after a relatively long storage time, and can be distributed and dissolved uniformly in the resin. With previously used amine auxiliary bases, there are obtained unpleasantly smelling products tending to cake together, which are contaminated by amine complexes which are also formed and which after a relatively long storage time can only be apportioned poorly, and which relative to the resin, have a relatively low degree of latency.

The potentially mixed coordinated metal complexes of the invention can be produced according to the following generally formulated, single-stage reaction, wherein the reactants are used in about stoichiometric quantities:

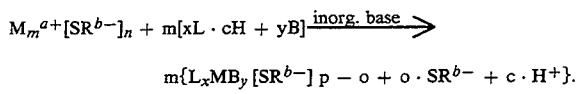

$$m\{L_xMB_y[SR^{b-}] p - o + o \cdot SR^{b-} + c \cdot H^+\}.$$

wherein M is a metal ion, SR is an acid radical of an organic or inorganic acid, B is a Lewis base and L is a chelating ligand, wherein m·a=b=n≧m(c·x)
x·c≦a
n/m=p
m·o≦n and
a=an integer of 1–8,
b=an integer of 1–3,
c=an integer of 0–4,
m=an integer of 1–3,
n=an integer of 1–8,
o=an integer of 0–8,
x=an integer of 0–4,
y=an integer of 8–15, preferably 9–11, and x+y+(p−o)<16, preferably x+y+(p−o)<12.

As the metal ion (M$^{a+}$), any complex-forming metal ion in principle can be used but preferably the ions of the second and third main group of the periodic system of elements as well as the ions of the sub-group elements are used. Among the preferred metal ions are cobalt, nickel, iron, zinc or manganese ions which are used in the form of inexpensive metal salts in the production of the complexes of the invention.

Examples of suitable metal salts are copper (I) and (II) salts such as copper chloride, copper bromide, copper fluoride, copper nitrate, copper fluoroborate, copper sulfate, copper acetate, copper trifluoro acetate, copper stearate, copper octoate, copper methacrylate, copper malonate, copper benzoate; nickel salts such as nickel chloride, nickel fluoride, nickel sulfate, nickel fluoroborate, nickel tallate, nickel stearate or nickel salts of other organic acids, such as ricinoleic acid; calcium salts such as calcium chloride, calcium bromide; cobalt salts such as cobalt chloride, cobalt fluoride, cobalt nitrate, cobalt sulfate, cobalt octoate, cobalt fluoroborate, cobalt stearate; zinc salts such as zinc bromide, zinc chromate, zinc chloride, zinc stearate, zinc octoate, zinc ethylhexoate; mercury salts such as mercury bromide or chloride; zirconium salts such as zirconium sulfate or zirconium chloride; indium salts such as indium fluoro-borate; silver salts such as silver nitrate; chromium salts such as chromium chloride; manganese salts such as manganese chloride, manganese sulfate; tin salts such as tin chloride, cadmium salts such as cadmium chloride; iron salts such as iron chloride, titanium salts such as titanium chloride; vanadium salts such as vanadium chloride, antimony salts such as antimony chloride and the like.

It is understood, that the listed salts are only a small portion of the metal salts usable in the process. For the production of the curing catalysts of the invention, cost-effective inorganic salts are preferred. However, well suited are also all salts of organic acids which have a pK value of approximately 1.2 to 5.7 (relative to a 0.1 N solution) and specifically those of acetic acid, oxalic acid, lactic acid, tartaric acid, malic acid, fumaric acid, malonic acid or of other suitable organic acids. Accordingly, all acid radicals described above are also considered as acid radicals (SR) in the equation.

In principle as the chelating ligand L, all other organic compounds which have at least two atom groupings with free electron pairs or electron gaps for forming complex compounds can be used. Examples of these are dioximes, α- and β-hydroxycarbonyl compounds, thus hydroxy carboxylic acids, ketones, aldehydes and their analogs or enolizable 1,3-diketones, but also CH-acids, Lewis bases such as malonic acid diester or dinitrile, acetoacetic ester or cyanoacetic ester. Preferred chelating ligands are acetylacetone, benzoylacetone and their homologs, dipivaloylmethane or dimethylglyoxime.

In the metal complex compounds according to experience, Lewis bases (B) can be all nucleophilic molecules or ions which have a lonely electron pair. Examples are pyridine, pyrimidine or imidazole compounds, ethers, including cyclic ethers, such as tetrahydrofuran, aliphatic and aromatic alcohols, ketones, thioethers or mercaptans. But Lewis bases in the complexes of the formula $L_xMB_y$ can also be CH-acidic compounds which are present as Lewis bases, i.e., CH-acidic compounds in which a proton is split off. Examples of such CH-acidic Lewis bases are CH-acidic pyridines or nitromethane.

The charge equalization of the metal cations of the metal complex compounds to be used can take place through the ligands themselves as well as also through ionic Lewis bases. It is therein understood that the number of charge-carrying ligands is reduced if the complex comprises ionic Lewis bases.

A further implementation of the complexes produced by the invention resides in that the CH-acidic Lewis bases are bound through nitrogen and/or oxygen and/or sulfur and/or phosphorus atoms, or hydrogen bridges to the metal chelate compound.

The conversion of the starting compounds takes place at temperatures from 0° to 200° C., preferably at 20° to 80° C. For carrying out the process, the metal salt, the organic compound acting as chelating ligand and the Lewis base to be bound additionally are mixed together with the inorganic base or the salt acting as a base with water and optionally a solubilizer and brought to the desired temperature. Then, the high energy input can take place through high-speed stirrers such as through an Ultra Turrax, through mixing sirens or, microwave, ultrasound or laser beam sources or in other ways. In this way, the time the reaction mixture spends in the reactor can be reduced to a few minutes and the complexes which crystallize out immediately after they are formed, can be separated.

Due to the short reaction time and the rapid crystallization of the product, the conversion can be carried out continuously in a simple manner wherein the separation of the product takes place in conventional manner, for example through filtering, centrifugation or sedimentation.

As a reaction vessel with appropriate internal fittings for the high energy input, in cascade continuously operated flow tube reactors of different implementations can be used which, in the simplest case, can be preceded by small mixing chambers as well as also a loop-type bubble column with forced circulation or simple stirred-tank reactors with or without internal fittings, but equipped with a suitable possibility for energy input. Of particular advantage for this continuous process, is the possibility of being able to rapidly crystallize the desired complexes out of the dilute aqueous solutions without prior concentration and to obtain an especially pure product which can be used as a polymerization or curing catalyst without further processing. The product is fine-grained and pourable, which even after relatively long storage, does not tend to cake together. If the separated complex is not to be used immediately, it is recommended that it be dried and this can take place continuously in a thin film drier or blade drier.

The process parameters are especially advantageous if the metal ions in the reaction solution have concentrations of approximately 6 to 70% of the maximum solution concentration achievable through the salt used and the particular complexing agent, i.e. chelating agent and Lewis bases, are added in stoichiometric quantities. Depending on the desired complex, the latter are added so that the molar ration of metal ion, chelating ligand and Lewis base is 1:(1-4):(2-16), preferably 1:(1-4):(8-12). In the production of the reaction mixture, the concentration of the individual reaction partners and that of the auxiliary base must be selected so that a dilute solution is obtained whose total concentration does not exceed the solubility equilibrium. A fast complex formation occurs if the concentration of the auxiliary base corresponds to that of the Lewis base.

As solubilizers for the chelating agents or Lewis bases having low solubility, organic solvents can be added such as ethanol, propanol, dimethylformamide or others in amounts of 0.01 to 20 percent by weight, preferably 5 to 10 percent by weight, relative to the total mixture.

If complexes are to be produced with especially high coordination numbers, it is possible, after a given reaction time which allows the conclusion that all reaction partners present in the solution have completed the reaction, to add further chelating ligands or further Lewis bases and to expose the reaction solution again to a high energy input. In this way, the coordination number can be further increased, in other words, the second coordination sphere can be occupied in which customarily water molecules are bound in hydrate-containing crystals. This can be carried out especially advantageously in a flow tube reactor with multiple feed possibilities.

Through the described process inter alia, the following complexes can be produced: bis (benzoylacetonato) nickel (II) diimidazole, bis (benzoylacetonato) iron (II) dipyrazole, bis (benzoylacetonato) zinc (II) tetrahydrate, bis (trifluorobenzoylacetonato)-cobalt (II) tetrabenzimidazole and bis (hexafluoroacetylacetonato)-nickel (II) tetrapyrazole.

Because they are fine-grained, the neutral complexes produced can be especially readily dissolved in polymer mixtures based on epoxy resins or polyurethane resins to be cured and, after the onset of the curing reaction, lead to especially short curing times. The curing of the resins takes place at temperatures between 40° and 180° C., preferably 60° to 140° C.

Curing experiments with complex salts which have an especially high coordination number or with such salts in which the Lewis bases are bound in a second coordination sphere, show two curing stages, especially when low complex concentrations are used. This is of particular advantage since resin systems for the production of precured products can be made available whose pre- and postcuring can be brought about by only one curing catalyst. In addition, through this possibility, an interaction between the previously used catalyst systems for precuring and postcuring is avoided so that precisely for this reason, the new complex compounds are effective in low concentrations as catalyst for both curing stages of precured products.

The neutral complex salts can be used in concentrations of 0.01 to 50 percent by weight, preferably 0.1 to 20 percent by weight relative to the total resin mixture, for the curing of epoxy resin products as well as also of polyurethanes.

All epoxy compounds with more than one epoxy bonding can be cured through the catalysts of the invention. Preferred epoxy compounds are polyphenol glycidyl ethers, for example epoxidized novolaks or the reaction products from epichlorohydrin and bisphenol A or bisphenol F. Epoxy resins of this type have an epoxy equivalent of 160 to 500. The above listed polyfunctional epoxy compounds, including the term epoxy resin, can be precured and postcured or directly cured individually or in mixtures, optionally in the presence of solvents. But they also can be used in a mixture with monoepoxides (so-called reactive thinners). Equally well suited are also glycidylized anilines.

The catalysts of the invention are also suitable in the described manner as curing agents for all mixtures cross-linked to polyurethanes which comprise monomers, oligomers or prepolymers with free isocyanate groups. Corresponding mixtures are known from Kunststoff Handbuch, Vol. 7, Polyurethanes, Becker et al, Editor Dr. Günter Oerterl, Carrl Hanser Verlag, 1983. Among these mixtures are mixtures with other polymers such as polycarbonates, polyacrylates, unsaturated polyester resins, preferably with polyepoxides.

Depending on the choice of the curing catalysts to be used, after the addition of the catalysts, resins having storage stability or resins precuring at low temperatures are obtained which, after forming, cure at increased temperatures between 80° to 200° C., preferably 100° to 150° C.

This curing behavior can be utilized to produce adhesion-free prepregs or prepregs of a defined tack with storage stability which, after the final curing, have especially high product qualities since it is possible to work without solvents with the curing catalysts of the invention. In addition, they can very easily be mixed uniformly with the resin mixtures.

In the following examples, there are described several preferred embodiments to illustrate the invention. However, it is to be understood that the invention is not intended to be limited to the specific embodiments.

EXAMPLE 1

1 mole of nickel (II) nitrate. 6 $H_2O$ was thoroughly mixed with 2 moles of benzoylacetone, 2 moles of imidazole and 2 moles of potassium hydroxide in a stirred tank reactor containing 500 ml of a methanol/water mixture in a ratio of 3:2 with an Ultra Turrax (20,000 rpm). After a short reaction time, the bis (benzoylacetonato)-nickel (II) diimidazole dimethanol was formed with a yield of 99%. After filtration, the complex was present as a powder with a grain size <10 μm.

| Analysis: | | theoretical [%] | calculated [%] |
|---|---|---|---|
| | Ni | 10.2 | 10.1 |
| | C | 58.0 | 58.2 |
| | H | 5.9 | 5.8 |
| | N | 9.7 | 9.9 |

EXAMPLE 2

1 mole of cobalt (II) chloride. 6 $H_2O$ was weakly stirred for 10 minutes with 2 moles of chinaldine acid, 2 moles of pyridine and 1 mole of $Na_2CO_3$ in 500 ml of an ethanol/water mixture in a ratio of 1:1 under the effect of ultrasound. The bis (chinaldato)-cobalt (II) dipyridine was formed with a yield of 99.5%.

| Analysis: | | theoretical [%] | calculated [%] |
|---|---|---|---|
| | Co | 10.5 | 10.5 |
| | C | 64.2 | 64.3 |
| | H | 3.9 | 4.0 |
| | N | 10.0 | 10.2 |

EXAMPLE 3

29 moles of cobalt (II) nitrate hexahydrate were intimately mixed with 43.2 g of trifluorobenzoyl acetone, 47.5 g of benzimidazole, and 8 g of NaOH in 100 ml of a mixture of acetone and water in a ratio of 1:1 while stirring at 1,000 rpm. After 15 minutes, the complex bis (trifluorobenzoyl acetonato)-cobalt (II) tetrabenzimidazole precipitated with a yield of 96%.

| Analysis: | | theoretical [%] | calculated [%] |
|---|---|---|---|
| | Co | 6.1 | 6.0 |
| | N | 11.7 | 11.5 |
| | C | 47.5 | 47.7 |

EXAMPLE 4

29.0 g of nickel (II) nitrate hexahydrate were intimately mixed at 500 rpm with 41.5 g of hexafluoro acetone, 30 g of pyrazole and 11.2 g of KOH in 90 ml of water with 10 ml of methanol. After stirring for 15 minutes, the complex bis (hexafluoroacetylacetonato) nickel (II) tetrapyrazole had been formed with a yield of 97%.

| Analysis: | | theoretical [%] | calculated [%] |
|---|---|---|---|
| | Ni | 7.9 | 8.1 |
| | N | 15.0 | 14.8 |

-continued

| Analysis: | theoretical [%] | calculated [%] |
|---|---|---|
| C | 35.4 | 35.5 |

EXAMPLE 5

The production of prepreg material was effected by known processes of wet technology or the hot melt process. The catalyst was intimately mixed into the diglycide ether of bisphenol-A (Rütapox 0164). If the mixture was processed through wet technology, the solvent was methyl ethyl ketone. The resin content of the prepreg following either processing method was 50 percent by mass and the flow of the resin was 30 percent by mass. The prepreg storage stability was depicted at room temperature in comparison to the pure Lewis base. Storage stability was not given if the flow of the resin was <10 mass percent.

|  | Catalyst of Example 1 | Lewis base Imidazole | Comparison Experim. hexa (imidazole) Ni (II) Dinitrate |
|---|---|---|---|
| Wet Technology | 48 days | 2 days | 7 days |
| Hot melt | 47 days | 1 hour | 7 days |

|  | Example 2 | Pyridine | Hexa(pyridine)-Ni (II) Dinitrate |
|---|---|---|---|
| Wet Technology | 73 days | 5 days | 7 days |
| Hot melt | 69 days | 12 hours | 7 days |

Various modifications of the composition and process of the invention may be made without departing from the spirit or scope thereof and it is to be understood that the invention is intended to be limited only as defined in the appended claims.

What is claimed is:

1. A process for the preparation of a neutral metal complex salt with additional coordinated ligands comprising reacting a complex-forming metal salt of the metal M as defined below with a chelating ligand and a Lewis base in water and the optional presence of a solubilizer and an inorganic auxiliary base which forms a soluble salt with the acid radical of the metal salt in stoichiometric amounts while inputting high energy to form the neutral complexes and recovering the product in fine crystalline form, the reaction being represented by the equation:

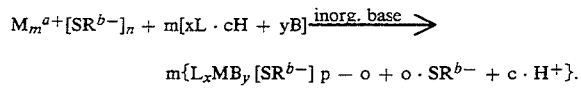

$$M_m{}^{a+}[SR^{b-}]_n + m[xL \cdot cH + yB] \xrightarrow{\text{inorg. base}}$$
$$m\{L_xMB_y[SR^{b-}]\, p - o + o \cdot SR^{b-} + c \cdot H^+\}.$$

wherein M is a metal ion selected from the group consisting of cobalt, nickel, iron, zinc, manganese, copper, mercury, zirconium, tin, cadmium, titanium, vanadium, indium, silver, chromium and antimony, SR is an acid radical of an organic or inorganic acid, B is a Lewis base and L is a chelating ligand, wherein $m \cdot a = b \cdot n > m(c \cdot x)$
$x \cdot c < a$ and $n/m = p$, $m \cdot o < p$, and
a = an integer of 1-8,
b = an integer of 1-3,
c = an integer of 0-4,
m = an integer of 1-3,
n = an integer of 1-8,
o = an integer of 0-8,
X = an integer of 0-4,
y = an integer of 8-15.

2. The process of claim 1, wherein y is an integer from 9 to 11 and the sum of $x+y+(p-o) \leq 12$.

3. The process of claim 1, wherein the input of energy is effected by high shearing forces caused in the dissolver by mixing sirens or extremely high stirrer speeds.

4. The process of claim 1, wherein the energy input is brought about by ultrasound, microwave or laser beam.

5. The process of claim 1, wherein the reaction is carried out at temperatures between 0° and 150° C.

6. The process of claim 1, wherein the reaction is carried out at temperatures between 20° and 80° C.

7. The process of claim 1, wherein the solubilizer is ethanol, propanol or dimethylformamide in an amount of 0.01 to 20 percent by weight of the total mixture.

8. The process of claim 1, wherein the solubilizer is ethanol, propanol or dimethylformamide in an amount of 5 to 10 percent by weight of the total mixture.

9. The process of claim 1, wherein the inorganic auxiliary base is NaOH, KOH, Ca(OH)$_2$, Mg(OH)$_2$ or basic salts selected from the group consisting of sodium acetate, sodium carbonate and potassium carbonate.

10. The process of claim 1, wherein the concentration of the inorganic auxiliary base is the same as that of the Lewis base.

11. The process of claim 1, wherein the chelating ligand is selected from the group consisting of dioximes, α- and β-hydroxycarbonyl compounds, hydroxy carboxylic acids, ketones, aldehydes and their analogs or enolizable 1,3 diketones, dipivaloyl methane or dimethyl glyoxime, acetic acid, oxalic acid, lactic acid, tartaric acid, malic acid, fumaric acid, malonic acid or CH-acidic Lewis bases.

12. The process of claim 1, wherein the Lewis base is selected from the group consisting of pyridine, pyrimidine, imidazoles, ethers, aliphatic or aromatic alcohols, ketones, thioethers, mercaptans, CH-acidic pyridine and nitromethane.

13. The process of claim 1, wherein the reaction is effected continuously.

14. A neutral metal complex salt produced by the process of claim 1.

* * * * *